United States Patent [19]

Czuba et al.

[11] 4,391,029

[45] Jul. 5, 1983

[54] CATHETER HUB ASSEMBLY

[75] Inventors: Leonard F. Czuba, Lombard; Dean G. Laurin, Lake Zurich, both of Ill.

[73] Assignee: Baxter Travenol Laboratories Inc., Deerfield, Ill.

[21] Appl. No.: 143,072

[22] Filed: Apr. 24, 1980

Related U.S. Application Data

[62] Division of Ser. No. 970,609, Dec. 18, 1978, abandoned.

[51] Int. Cl.³ .................. B23P 11/02; B29C 13/00
[52] U.S. Cl. .......................... 29/450; 29/525; 264/230; 604/283
[58] Field of Search ............. 29/450, 525; 264/230; 128/214.4

[56] References Cited

U.S. PATENT DOCUMENTS

| | | | |
|---|---|---|---|
| 3,454,006 | 7/1969 | Langdon | 128/214.4 |
| 3,469,579 | 9/1969 | Hubert | 128/214.4 |
| 3,500,828 | 3/1970 | Padhora | 128/214.4 |
| 3,526,683 | 9/1970 | Heslop et al. | 264/230 X |
| 3,802,433 | 4/1974 | Raven | 128/214.4 |
| 3,861,972 | 1/1975 | Glover et al. | 128/214.4 X |
| 3,929,541 | 12/1975 | Spears et al. | 156/304.6 X |
| 4,095,598 | 6/1978 | Tschanz et al. | 128/214.4 |
| 4,191,185 | 3/1980 | Lemieux | 128/214.4 |

*Primary Examiner*—Charlie T. Moon
*Attorney, Agent, or Firm*—Paul C. Flattery; John A. Caruso; Garretson Ellis

[57] ABSTRACT

A catheter is provided with an improved hub assembly. The catheter defines an end which, in turn, defines a relatively enlarged transverse dimension for the catheter wall and a thickened annular lip, when compared with an adjacent portion of the catheter. A catheter hub defines a bore portion, the bore portion in turn defining a relatively constricted portion and a relatively enlarged portion. The enlarged catheter end is positioned within the relatively enlarged portion of the bore, while the adjacent portion of the catheter is positioned within the relatively constricted portion of the hub. A rigid tubular funnel fits within the bore of the catheter. As a result of this the collapse and subsequent passage of the enlarged catheter end through the relatively constricted portion of the hub is prevented.

3 Claims, 4 Drawing Figures

CATHETER HUB ASSEMBLY

CROSS REFERENCE TO RELATED APPLICATION

This application is a division of U.S. Application Ser. No. 970,609 filed Dec. 18, 1978 now abandoned.

BACKGROUND OF THE INVENTION

Many catheters, particularly intravenous and arterial catheters, carry a separate hub on one end thereof for attachment of the catheter to a source of parenteral solution, blood or the like. A serious occasional problem which has been encountered with intravenous and arterial catheters is that, upon withdrawing of the catheter from an artery or vein, the hub separates from the catheter. On occasion the catheter has actually been lost in the cardiovascular system of the patient. Obviously, it is important to avoid even a very occasional occurence of this incident.

There are many ways of fitting a catheter into a hub. Adhesives or solvent bonding of the catheter tube to the hub may be used, and various friction fit attachments may also be used. However, these techniques have proven to be less successful for use in flexible catheters than the technique of this invention. Specifically, with the other bonding techniques the catheter and hub still can separate, especially with catheter materials which have low friction surfaces such as fluorocarbon plastics and silicone-lubricated elastomers, and hydrogel-coated catheters.

In accordance with this invention the bond between the catheter hub and the catheter itself is stronger than the tensile strength of the catheter, so the catheter can actually break before losing its bond with the hub. This can be even when catheter materials are used which are stronger than silicone rubber.

DESCRIPTION OF THE INVENTION

The catheter assembly of this invention is provided having an improved catheter hub, which comprises: a tubular catheter defining an end which in turn defines a relatively enlarged transverse dimension for the catheter wall and a thickened annular lip, when compared with an adjacent portion of said catheter.

A catheter hub defines a bore portion, and the bore portion in turn defines a relatively constricted portion and a relatively enlarged portion. The enlarged catheter end is positioned within the relatively enlarged portion of the bore while the adjacent portion of the catheter is positioned within the relatively constricted portion of the bore.

Preferably, a rigid, tubular funnel member may be positioned within the bore of the catheter. The funnel member may define an enlarged funnel section positioned within the relatively enlarged portion of the hub. The funnel member may be advantageously made of stainless steel, rigid plastics, such as polypropylene, polyethylene, or various nylons which are of lower cost than stainless steel, or high friction plastics in order to assure even lower probability that the catheter may pull out before the ultimate strength of the catheter is approached. The commercially available CENTRASIL catheter sold by Travenol Laboratories, Inc. also uses a funnel member, but in a manner apart from the structure of this invention.

The result of the structure of this invention is that the collapse and subsequent passage of the enlarged catheter end through the relatively constricted portion of the bore is prevented upon attempted pulling of the catheter out of the hub. Instead, as stated above, a properly designed catheter in accordance with this invention can actually be broken apart by pulling, without the end being pulled out of the hub, thereby having the advantage of the ultimate breaking resistance of the material being available for removing the catheter from the patient.

Preferably, the funnel member may be made of stainless steel or the like, and is essentially entirely positioned within the catheter bore, serving to enclose the enlarged end of the catheter between the hub and funnel.

The catheter may be made out of any desired material. However, preferably, it is contemplated to make the catheter out of a mixture of thermoplastic olefin-type polymers which may contain a chemically reactive cross-linkable or graftable silicone gum, for example as taught in the patent application of Dean G. Laurin, et al., Ser. No. 888,253, filed Mar. 17, 1978 now U.S. Pat. No. 4,196,731 issued Apr. 8, 1980, entitled "Silicone-Containing Thermoplastic Polymers for Medical Uses". Such materials can have relatively high tensile strength.

Alternatively, other materials can be used as a substitute for the material described above, i.e., fluorinated poly(ethylene-propylene), polytetrafluoroethylene, polyethylene, polyvinylchloride, polyurethane, EVA, styrene-rubber block copolymers, block copolyesters, and similar materials. The polyurethane and other materials may be externally lubricated with silicone oil, glycerine, or the like. The advantages of external lubricants can be utilized in this invention without significantly weakening the adhesion of the catheter to the hub, since the adhesion in this invention depends upon bulk deformation rather than friction.

In general, the term "flexible" as used in this application is intended to include the term "semi-flexible" and "semi-rigid", including relatively stiff plastics which nevertheless are still flexible in the broad sense.

While the catheter of this invention is specifically contemplated to be an IV catheter, it may also be used in arterial catheters, or any other desired type of catheter.

Figure 3:
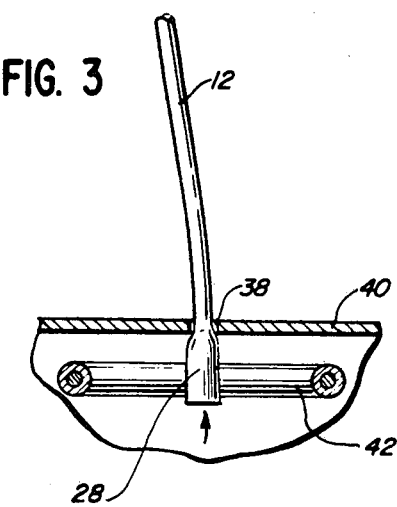
FIG. 3 is an elevational view showing a portion of the catheter to be assembled with a hub in accordance with this invention in the process of formation of its relatively enlarged transverse end.

Referring to the drawings, catheter assembly 10 is shown which comprises a catheter 12, which may be made of a thermoplastic material such as described above, or, alternatively, polyethylene, or a similar material. Silicone rubber can also be used.

Catheter hub 14 may be of generally conventional design, containing attachment wings 16 and a bore 18 which, in turn, is subdivided into a relatively constricted portion 20 and a relatively enlarged portion 22. A rigid tubular funnel member 23 which has an enlarged funnel section 24, and which carried a tubular section 26, may be positioned within the bore of catheter 12 as shown in FIG. 2.

Figure 4:
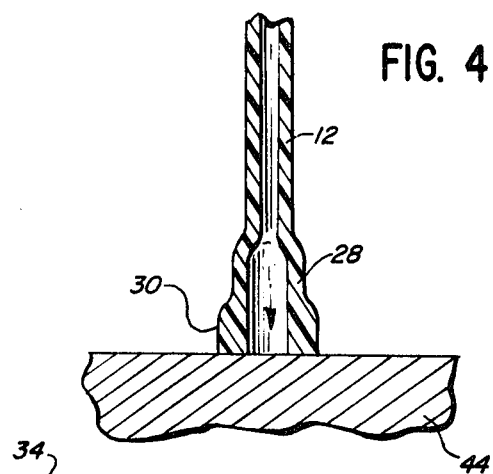
FIG. 4 is an elevational view, taken partly in section, of the enlarged end of the catheter of FIG. 1 in a further processing step for forming the thickened annular lip.
Figure 2:
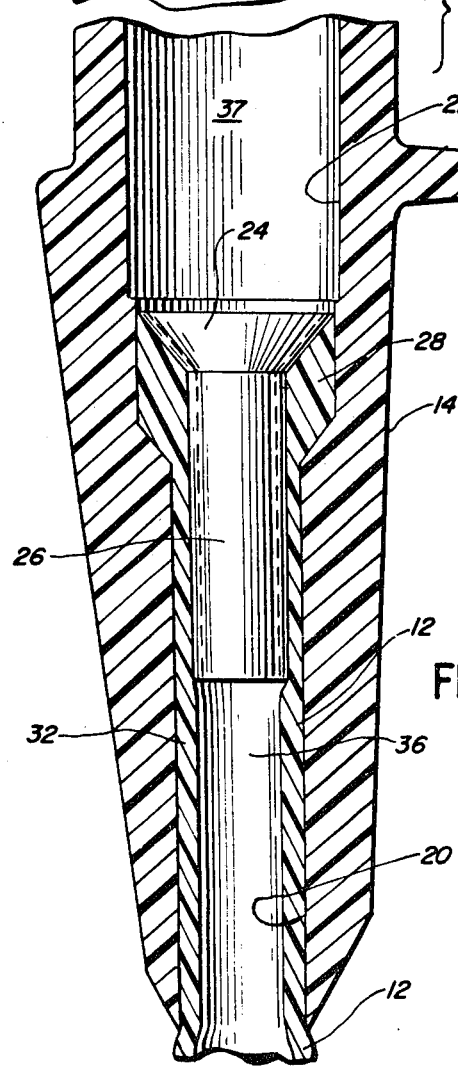
FIG. 2 is an enlarged longitudinal sectional view of the hub of the catheter of this invention after assembly.

The end 28 of catheter 12 defines a relatively enlarged transverse dimension for the catheter wall (as shown in FIGS. 2 and 4), and also a thickened annular lip 30 at the catheter end.

As shown in FIG. 2, as the respective parts are assembled, at least a substantial portion of the enlarged transverse end 28 with the thickened lip 30 occupies the enlarged bore portion 22 of the hub 14, while the adjacent portion 32 of catheter 12 passes through the relatively constricted bore portion 20, with the catheter 12 projecting out of the bottom of hub 14 in a normal manner.

Funnel member 23 is then forcefully inserted through outer end 34 of the hub into the bore 36 of catheter 12, with the tubular portion 26 of the funnel extending through catheter 12 into the relatively constricted bore portion 20 of hub 14, while the funnel section 24 itself resides in the relatively enlarged bore portion 22 to define an annular space and to press relatively enlarged catheter end 28 into the approximate shape of that annular space. It is preferable for the width of the widest portion of funnel section 24 to essentially equal the width of relatively enlarged bore portion 22, being just sufficiently smaller if necessary to permit insertion into enlarged bore portion 22.

As can be seen, a still further enlarged bore portion 37 may also be provided to provide a fitting for a connector or the like of a fluid conduit.

As a result of the above, the thickened, stressed end 28 generally assumes a harder characteristic than the remaining portions of the catheter because it is thicker. Accordingly, when catheter 12 is pulled in an attempt to yank it out of the hub 14, the enlarged portion 28 of catheter 12 serves as a resistant member, which for all practical purposes prevents the removal of the catheter from the hub. Instead, the catheter can be expected to break first. The presence of funnel 24 serves to enhance the strength of the connection between the hub and the catheter, since it prevents collapse of thickened end 28, which would facilitate its removal through the constricted bore portion 20.

The particular shape of end 28 of the catheter may be formed in the manner illustrated in FIGS. 3 and 4 in the case where a stressed thermoplastic material is used for catheter 12. The extruded catheter tube 12 is placed through an aperture 38 in a plate member 40, which generally serves to protect the majority of the length of the catheter from the heat of heating coil 42, or other heating means.

The exposed end 28 of the catheter is heated by the heating coil 42, which may be a standard ring-shaped heating member, causing end 28 to shorten in length and to thicken in width as stresses are relieved in the heated portion of the catheter.

Alternatively, hot water, oil or the like may be used as a substitute heat source for the air heating step specifically illustrated in FIG. 3.

Thereafter, plate 40 may be taken away from the heating coil and catheter 12 removed from aperture 38. Then, catheter 12 is preferably pressed against the surface of cool plate 44 while the plastic is of a temperature of about 150° C., or another temperature above the softening temperature of the catheter material, to define the thickened annular lip 30 at the extreme end of catheter 12.

Alternatively, end 28 of catheter 12 may be heat formed in a mold or die to the proper shape, if desired.

Figure 1:
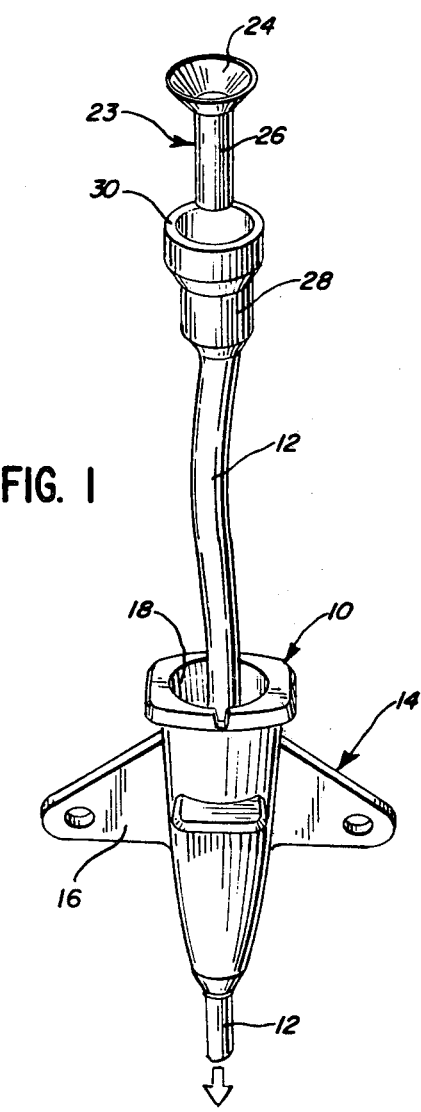
FIG. 1 is a perspective exploded view of the parts of the catheter of this invention prior to assembly.

The resulting catheter is then assembled in the manner illustrated in FIG. 1, and brought together as described above and as shown in FIG. 2, to provide a catheter having an extra strong hub.

Specifically, a catheter having an outer diameter along its unthickened wall of 0.069 inch and an inner diameter of 0.040 inch may be mounted in accordance with this invention in hubs as shown herein, to withstand a 5 to 7 pound pull without separation of the hub from the catheter. On the other hand, similar catheters not using the invention of this application tend to separate from their hubs with as little as a two pound pull.

This invention can also be used for connecting other tubing besides catheters, for example for connecting tubing for blood dialyzer or oxygenator circuits, or for connecting peristaltic pump tubing.

The above has been offered for illustrative purposes only and is not intended to limit the invention of this application, which is as defined in the claims below.

That which is claimed is:

1. The method of forming an end having a plurality of areas of increasing wall thickness on a heat recoverable stressed thermoplastic tubular catheter, which comprises: heating the end of the tubular catheter to cause it to spontaneously reduce its length and increase its wall thickness and inner diameter as stresses are relieved in the heated portion of said catheter, while not exposing the remainder of said catheter to heat, and thereafter pressing the end of said catheter at at least its softening temperature against a flat surface to form a thickened annular lip about the catheter end.

2. The method of claim 1 in which said catheter end projects through an aperture in a partition and is heated by radiant heat, while the partition shields the remainder of said catheter from said radiant heat.

3. The method of claim 1 in which said catheter is thereafter placed in a catheter hub having a bore which defines relatively constricted portion and a relatively enlarged portion, said catheter end being positioned within the relatively enlarged portion, while positioning the adjacent portion of the catheter within the relatively constricted portion of the hub, and thereafter fancing a rigid, tubular funnel member having an enlarged funnel section within the bore of said catheter, in which the enlarged funnel section of the funnel member is positioned within the relatively enlarged bore portion of the hub.

* * * * *